(12) United States Patent
de Hoog et al.

(10) Patent No.: US 11,497,455 B2
(45) Date of Patent: Nov. 15, 2022

(54) PERSONALIZED MONITORING OF INJURY REHABILITATION THROUGH MOBILE DEVICE IMAGING

(71) Applicant: INTERNATIONAL BUSINESS MACHINES CORPORATION, Armonk, NY (US)

(72) Inventors: Julian de Hoog, Greensborough (AU); Dwarikanath Mahapatra, Melbourne (AU); Rahil Garnavi, Macleod (AU); Fatemeh Jalali, Hawthorn East (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 694 days.

(21) Appl. No.: 16/589,046

(22) Filed: Sep. 30, 2019

(65) Prior Publication Data

US 2021/0093257 A1 Apr. 1, 2021

(51) Int. Cl.
*A61B 5/00* (2006.01)
*H04W 4/02* (2018.01)
(Continued)

(52) U.S. Cl.
CPC .......... *A61B 5/7425* (2013.01); *A61B 5/0075* (2013.01); *A61B 5/0522* (2013.01);
(Continued)

(58) Field of Classification Search
CPC ... A61B 5/7425; A61B 5/0075; A61B 5/0522; A61B 5/6898; A61B 5/7267;
(Continued)

(56) References Cited

U.S. PATENT DOCUMENTS

2009/0326383 A1* 12/2009 Barnes .................. A61B 5/442
850/1
2012/0120220 A1  5/2012 Al-Moosawi
(Continued)

OTHER PUBLICATIONS

Andriyan et al, ("Magnetic Subsurface Imaging Systems in a Smartphone Based on the Built-In Magnetometer", IEEE, vol. 53, No. 11, Nov. 2017) (Year: 2017).*

(Continued)

*Primary Examiner* — Amara Abdi
(74) *Attorney, Agent, or Firm* — Intelletek Law Group, PLLC; Gabriel Daniel, Esq.

(57) ABSTRACT

A method and system of diagnosing a medical condition of a target area of a patient using a mobile device are provided. One or more magnetic field images of a target area of a patient are received. One or more hyperspectral images of the target area of the patient are received. For each of the one or more magnetic field images and the one or more hyperspectral images, a three-dimensional (3D) position of the mobile device is tracked with respect to the target are of the patient. A 3D image of the target area is generated based on the received one or more magnetic field images, one or more hyperspectral images, and the corresponding tracked 3D position of the phone with respect to each image. A medical condition of the target area is diagnosed or monitored based on the generated 3D image.

20 Claims, 6 Drawing Sheets

(51) Int. Cl.
| | |
|---|---|
| *G06T 15/08* | (2011.01) |
| *G06T 5/00* | (2006.01) |
| *G06T 5/50* | (2006.01) |
| *G16H 30/40* | (2018.01) |
| *G16H 50/20* | (2018.01) |
| *A61B 5/0522* | (2021.01) |
| *H04N 5/232* | (2006.01) |

(52) U.S. Cl.
CPC .......... *A61B 5/6898* (2013.01); *A61B 5/7267* (2013.01); *G06T 5/002* (2013.01); *G06T 5/50* (2013.01); *G06T 15/08* (2013.01); *G16H 30/40* (2018.01); *G16H 50/20* (2018.01); *H04N 5/23222* (2013.01); *H04W 4/026* (2013.01); *A61B 2562/0219* (2013.01); *G06T 2207/10036* (2013.01); *G06T 2207/20081* (2013.01); *G06T 2207/30008* (2013.01); *G06T 2207/30088* (2013.01); *G06T 2207/30168* (2013.01)

(58) Field of Classification Search
CPC .......... A61B 2562/0219; A61B 5/0013; A61B 5/0035; G06T 5/002; G06T 5/50; G06T 15/08; G06T 2207/10036; G06T 2207/20081; G06T 2207/30008; G06T 2207/30088; G06T 2207/30168; G06T 2207/20084; G06T 7/0002; G06T 7/0016; G06T 7/55; G16H 30/40; G16H 50/20; G16H 50/30; G16H 80/00; H04N 5/23222; H04W 4/026

See application file for complete search history.

(56) References Cited

U.S. PATENT DOCUMENTS

| | | | | |
|---|---|---|---|---|
| 2016/0150976 | A1* | 6/2016 | Fang | A61B 5/015 600/474 |
| 2016/0157725 | A1* | 6/2016 | Munoz | H04N 5/2256 600/407 |
| 2016/0183879 | A1* | 6/2016 | Goldish | A61B 5/0077 600/407 |
| 2017/0202633 | A1 | 7/2017 | Liu | |
| 2018/0032682 | A1* | 2/2018 | Donalds | G16H 30/20 |
| 2018/0293350 | A1* | 10/2018 | Dimov | G16H 20/60 |

OTHER PUBLICATIONS

Jonathan et al, ("Hyperspectral imaging with near-infrared-enabled mobile phones fortissue oximetry", Proceeding of SPIE, 2018, San Francisco, California, United States) (Year: 2018).*

Benchoff, B. "High Speed Imaging of Magnetic Fields"; Hackaday (2018), 16 pgs.

Lin, J. et al., "Hyperspectral Imaging with Nearinfrared-Enabled Mobile Phones for Tissue Oximetry"; Proceedings of SPIE (2018); 12 pgs.

Shanmugam, P. et al., "Fundus Imaging with a Mobile Phone: A Review of Techniques"; Indian J. Ophthalmol. (2014); vol. 62:9, 7 pgs.

Skandarajah, A. et al., "Quantitative Imaging with a Mobile Phone Microscope"; PLOS One (2014); vol. 9:5; pp. e96906 (12 pgs).

Suksmono, A. B. et al., "Magnetic Subsurface Imaging Systems in a Smartphone Based on the Built-In Magnetometer"; IEEE Transactions on Magnetics (2017); vol. 53:11; 5 pgs.

Suksmono, A. B. et al., "Magnetic Imaging System in Smartphones Based on Built-In Magnetometer"; School of Electrical Engineering and Informatics, Institut Teknologi Bandung, Bandung, Indonesia (2017); 1 pg.

Zhao, Y. et al., "LMDD: Light-Weight Magnetic-Based Door Detection with Your Smartphone"; 44th International Conference on Parallel Processing (2015); 10 pgs.

* cited by examiner

PERSONALIZED MONITORING OF INJURY REHABILITATION THROUGH MOBILE DEVICE IMAGING

BACKGROUND

Technical Field

The present disclosure generally relates to mobile computing devices, and more particularly, to using mobile computing devices to identify or monitor a medical condition of a patient.

Description of the Related Art

In recent years, mobile wireless communications have become increasingly popular. Initial implementations of mobile wireless communications, for example in the form of cellular telephone networks, supported circuit switched voice communication services. The carriers developed short message service (SMS) technology to provide text and/or e-mail communications via the wireless communication networks. As the wireless communication networks have evolved to provide greater bandwidth and packet-based services, the industry has developed a variety of data services, such as email, web browsing, as well as a variety of services using multimedia message service (MMS) technology. Further, mobile devices have evolved to include an ever-increasing number of features, including WiFi and/or cellular data network-based internet access, global positioning system (GPS) capability, an accelerometer, a gyroscope, one or more cameras, light sensor, rotation vector sensor, gravity sensor, orientation sensor, etc. The advanced features support an ever-increasing range of uses of the mobile devices, such as web browsing, email communication, gaming, etc. As the features and capabilities of mobile devices are steadily increasing, mobile devices are rapidly becoming the central computer and communication device for many. The compact form factor of mobile devices allows them to be used almost anytime and anywhere.

SUMMARY

According to various exemplary embodiments, a mobile device, a non-transitory computer readable storage medium, and a method are provided to diagnose a medical condition of a patient. One or more magnetic field images of a target area of a patient are received. One or more hyperspectral images of the target area of the patient are received. For each of the one or more magnetic field images and one or more hyperspectral images, a three-dimensional (3D) position of the mobile device with respect to the target are of the patient is tracked. A 3D image of the target area is generated based on the received one or more magnetic field images, one or more hyperspectral images, and the corresponding tracked 3D position of the phone. A medical condition of the target area is diagnosed and/or monitored based on the generated 3D image.

In one embodiment, receiving one or more magnetic field images of the target area includes emitting a magnetic field by a transceiver of the mobile device onto the target area and receiving at least one of radio or magnetic signals from the target area in response to the emitted magnetic field of the transceiver. The magnetic signal from the target area may be received by a magnetic field sensor of the mobile device. Receiving one or more magnetic field images of the target area may further include, for each of the one or more magnetic field images, providing guidance on a user interface of the mobile device as to how to position the mobile device in 3D space with respect to the target area.

In one embodiment, receiving one or more hyperspectral images of the target area includes, for each hyperspectral image, controlling a light source of the mobile device, to emit light at one or more predetermined wavelengths; and recording a hyperspectral image of an anatomy of the target area by a camera of the mobile device. Receiving one or more hyperspectral images of the target area may further include, for each of the one or more hyperspectral images: providing guidance on the user interface as to how to position the mobile device in 3D space with respect to the target area.

In one embodiment, at least one of the one or more magnetic field images and at least one of the one or more hyperspectral images are taken concurrently from a same position in 3D space with respect to the target area.

In one embodiment, for each hyperspectral image, a quality of a resolution of the hyperspectral image is determined. Upon determining that the quality of the resolution of the hyperspectral image is below a predetermined threshold, the image is enhanced by way of a deep learning model.

In one embodiment, the 3D image is further based on one or more photographs taken by a camera of the mobile device.

According to one embodiment, a computer implemented method includes directing a transceiver of a mobile device to emit a magnetic field onto a target area of a patient. A signal is received in response to the emitted magnetic field. One or more magnetic field images of the target area are created. A light emitting source of the mobile device is controlled such that light is generated at one or more different wavelengths. One or more hyperspectral images of the target area are created in response to the light generated at the one or more different wavelengths. A 3D position of the mobile device is tracked with respect to the target area for each of the one or more magnetic field images and the one or more hyperspectral images. A 3D image of the target area is generated based on the created one or more magnetic field images, the one or more hyperspectral images, and the corresponding tracked 3D position of the mobile device. A medical condition of the target area is diagnosed and/or monitored based on the generated 3D image.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

DETAILED DESCRIPTION

Overview

Figure 1:
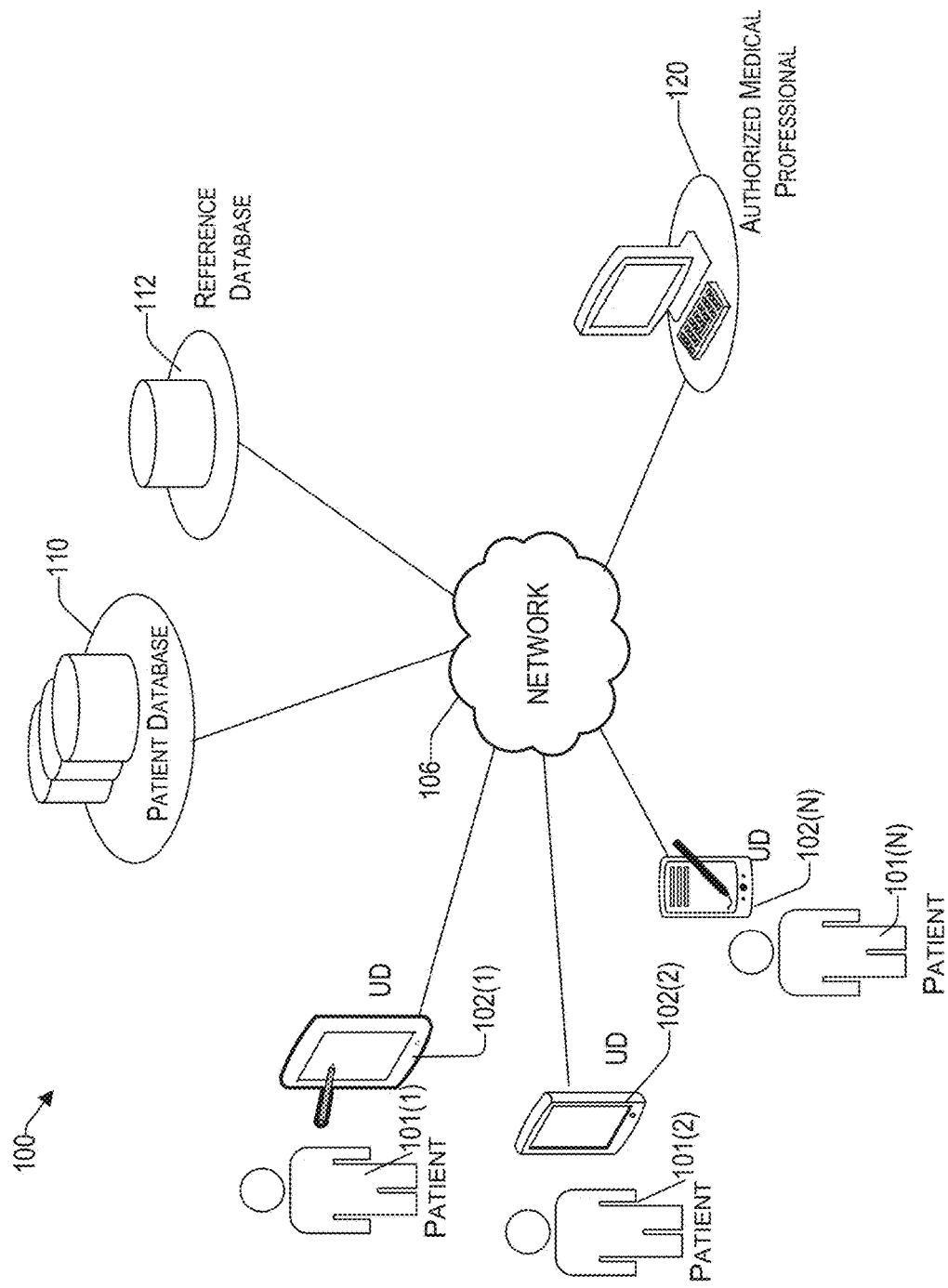
FIG. 1 illustrates an example architecture for implementing a system that provides medical imaging using a mobile device.

In the following detailed description, numerous specific details are set forth by way of examples in order to provide a thorough understanding of the relevant teachings. However, it should be apparent that the present teachings may be practiced without such details. In other instances, well-known methods, procedures, components, and/or circuitry have been described at a relatively high-level, without detail, in order to avoid unnecessarily obscuring aspects of the present teachings.

The present disclosure generally relates to medical imaging using a mobile device. Injuries or other external or internal health status, collectively referred to herein as a medical condition, can be determined by way of using various sensors that are available in a mobile device. These sensors can be used to generate images of not just what is visible externally on a user (e.g., patient), but also the underlying bones, tissues, and organs. The images can be used to generate a three-dimensional rendering of the anatomy of a target area of a patient.

Any kind of injury affects the quality of life as it limits the individual's ability to perform routine activities. During the recovery period, depending upon the seriousness of the injury, the patient may want to regularly consult a medical professional to determine how well he or she is recovering. Often visits to a professional medical facility may not be practical in various scenarios. For example, regular visits to a clinic may be inconvenient (e.g., particularly for the elderly); there may be delays in the availability of medical equipment, such as magnetic resonance imaging (MM) or CAT (CT) scan; there may be scheduling conflicts with daily routines; the procedures may be cost prohibitive; etc. During the period between visits to the medical professional, there may be no effective way to determine how well a particular medical condition (e.g., muscle, bone, tendon, organ, internal infection, etc.) is healing, since specialized medical equipment (which may only be available at a clinic) may be involved to image the anatomy of the subject medical condition. Such a situation poses the following challenges. Consequently, a patient's medical condition may not progress optimally or worsen by simply being unaware of the progress.

Accordingly, what is discussed herein are methods and systems of using mobile devices that are particularly configured to provide a personalized monitoring of a medical condition of a patient. A combination of sensors that are inherent in modern mobile devices are controlled in a specific way to transform the mobile device to be able to generate images of not just what is externally visible, but also the underlying bones, tissues, and organs, as well as their state of rehabilitation. In one embodiment, by combining acquired images using hyperspectral imaging and magnetic field images generated from the phone, along with the device's orientation in 3-dimensional (3D) space, and applying methods that stitch together features from separate images, it is possible to generate 3D models of the underlying bone, tissue or organ that provide significantly improved understanding of the underlying medical condition, and the progress of rehabilitation.

The techniques described herein may be implemented in a number of ways. Example implementations are provided below with reference to the following figures.

Example Architecture

FIG. 1 illustrates an example architecture 100 for implementing a system that provides medical imaging using a mobile device. Architecture 100 includes a network 106 that allows various mobile devices 102(1) to 102(n) of corresponding users 101(1) to 101(N), sometimes referred to herein as patients, to communicate with various components that are connected to the network 106, such as one or more patient database 110, reference database 112, and an authorized medical professional 120. The network 106 may be, without limitation, a local area network ("LAN"), a virtual private network ("VPN"), a cellular network, the Internet, or a combination thereof. For example, the network 106 may include a mobile network that is communicatively coupled to a private network, sometimes referred to as an intranet, which provides various ancillary services, such as communication with various application stores, databases, and the Internet. To facilitate the present discussion, network 106 will be described, by way of example only and not by way of limitation, as a mobile network as may be operated by a carrier or service provider to provide a wide range of mobile communication services and supplemental services or features to its subscriber customers and associated mobile device users 101(1) to 101(N). The network 106 allows users of the mobile devices 102(1) to 102(n) to communicate with each other and to receive data from or provide data to the patient database 110, reference database 112, and/or an authorized medical professional 120.

For purposes of later discussion, several mobile devices appear in the drawing, to represent some examples of the devices that may receive various services via the network 106. Today, mobile device's typically take the form of portable handsets, smart-phones, tablet computers, personal digital assistants (PDAs), smart watches, and laptops, although they may be implemented in other form factors, including consumer, and business electronic devices.

A mobile device 102(1) to 102(N) may have various applications stored in its memory that may have been downloaded from various application stores. Each mobile device that is subscribed to the medical imaging described herein, includes an application, sometimes referred to herein as the diagnosis engine, is operative to capture various images of a target area of a patient. For example, the target area may represent an injury, such as, without limitation, a skin tear, infection, bone fracture, ruptured tendon, etc. The diagnosis engine can control hardware that may be inherent in its corresponding mobile device to generate various signals, including magnetic fields of different predetermined strength and light at different wavelengths. The diagnosis engine further configures the mobile device to receive various signals in response to the emitted magnetic fields and light. The signals received in response to the magnetic fields generated by the mobile device are used to create a magnetic field image. In contrast to electric signals, which are influenced by the differently conductive tissue of the body and varying resistance of the skin before they can be recorded, the magnetic signals travel through the body almost without disturbance, thereby being able to observe structures below the skin of the patient.

The control of a light source of the mobile device, such as a light emitting diode (LED), may be used to create hyperspectral imaging of the target are of the patient. The hyperspectral imaging discussed herein uses a camera of a mobile device to collect and processes information from across an electromagnetic spectrum of the controlled light source of the mobile device. In this way, the camera of a mobile device can obtain the spectrum for each pixel in the image of a target area of the patient, with the purpose of identifying the underlying structure. For example, the camera of a mobile device collects information in the form of a set of images. Each image represents a narrow wavelength range of the electromagnetic spectrum, also known as a spectral band. These images are combined to form a three-dimensional $(x,y,\lambda)$ hyperspectral data array for processing and analysis, where x and y represent two spatial dimensions of the scene, and $\lambda$ represents the spectral dimension comprising a range of wavelengths. The relative position of the mobile device in 3D space with respect to the target area is recorded by the mobile device to later be able to construct a 3D image from the gathered images and corresponding positions.

Accordingly, both the magnetic field images and the hyperspectral images may be taken from different positions, guided by the mobile device. For example, the diagnosis engine may interact with a patient database 110 to determine the relevant target area of a patient, the range of magnetic fields, the light wavelengths, the number of images to take for each of the magnetic field imaging and hyperspectral imaging, and which positions in 3D space in relation to the target area of the patient. In one embodiment, the diagnosis engine uses various sensors, such as optical (e.g., camera), accelerometer, and/or gyroscope to provide guidance to the user holding the mobile device as to how to position and/or move the mobile device in 3D space to be capture the hyperspectral and magnetic field images, respectively. For example, for skin tears or infections, a predetermined set of wavelengths, magnetic fields, and/or a number of pictures may be taken, whereas for a bone fracture, a different set of wavelengths, magnetic fields, and/or number of pictures may be dictated.

In various embodiments, the magnetic field images and the hyperspectral images may be taken concurrently or separately. For example, the diagnosis engine may first provide guidance to move the mobile device in 3D space to complete the requisite magnetic field images from different positions while controlling the magnetic field generated. Upon determining that the magnetic field images are complete, the diagnosis engine stops generating a magnetic field and initiates control of the desired wavelength of light, while providing guidance to move the mobile device in 3D space to complete the requisite hyperspectral images. In another embodiment, the order of types of images taken can be reversed or performed concurrently. In one embodiment the magnetic field used and the wavelengths of light used, based on the condition being investigated, may be provided by the patient database 110, discussed in more detail below.

In various embodiments, the guidance to position the mobile device in 3D space with respect to the target area of the patient may be provided via the speakers of the mobile device as voice instructions (e.g., "please gradually move closer to the elbow while rotating the phone to the left"), audible tone (e.g., beeps), messages on a display of the mobile device, augmented reality on the display of the mobile device, haptic signals, or any combination thereof.

By combining the acquired images from different positions with respect to the target area of the patient using hyperspectral imaging and magnetic field images generated from the mobile device, and applying methods that stitch together features from separate images, the teachings herein generate 3D models of the underlying bone, tissue, and/or organ, which can provide a significantly improved understanding of the underlying medical condition and the progress of rehabilitation. In some embodiments, the results may be saved in the patient database 110 and/or provided to an authorized medical professional 120. For example, if the progress is below a predetermined threshold (e.g., not progressing as reference expected data when compared to expected data received from a reference database 112), an electronic message is sent to the authorized medical professional 120, which may include the generated 3D image of the target area of the patient.

As mentioned above, the architecture 100 may include a patient database 100 that is operative to provide its account holders (e.g., subscribers to the diagnosis engine service discussed herein) on-line access to a variety of information related to a user's (e.g., patient's) account, such as existing medical conditions, medical issues to monitor, specific target areas of the patient, and the like. The patient database may maintain an ongoing history of all prior information related to an injury being monitored, as well as a database of past scans. Over time, and across a growing user base, the patient database 110 can learn to identify relative progress of different medical conditions (e.g., injuries). This learning could for example be in the form of machine learning where rehabilitation progression is modelled as a function of multiple inputs, such as gender, age, degree of injury severity, as well as any other relevant features that may be correlated to the rate of rehabilitation. Depending upon the target application and the number of patient records, in one embodiment, a random forest classifier/regressor (for less patient data) or a neural network architecture (for large number of records) may be used. Further it can provide a mobile device (e.g., 102(1)) of a patient (e.g., 101(1)) and/or an authorized medical professional 120 various information, such as, without limitation, (i) a condition/disease affecting the area; (ii) a severity score of the disease; (iii) a change in status compared to a previous scan; (iv) disease progression statistics compared to other patients having a similar condition; (v) recommended future steps (e.g., whether and when to visit a medical professional). In one embodiment, the features of the patient database 100 are part of the diagnosis engine of the mobile device.

While the patient database 110 and reference database 112 have been illustrated by way of example to be on different platforms, it will be understood that in various embodiments, their functionality described herein can be combined or even be part of a mobile device. In other embodiments, these computing platforms may be implemented by virtual computing devices in the form of virtual machines or software containers that are hosted in a cloud, thereby providing an elastic architecture for processing and storage. Each of the databases and computing devices discussed herein are compliant with the Health Insurance Portability and Accountability Act (HIPAA), which sets the standard for protecting sensitive patient data.

Example Mobile Device

Figure 2:
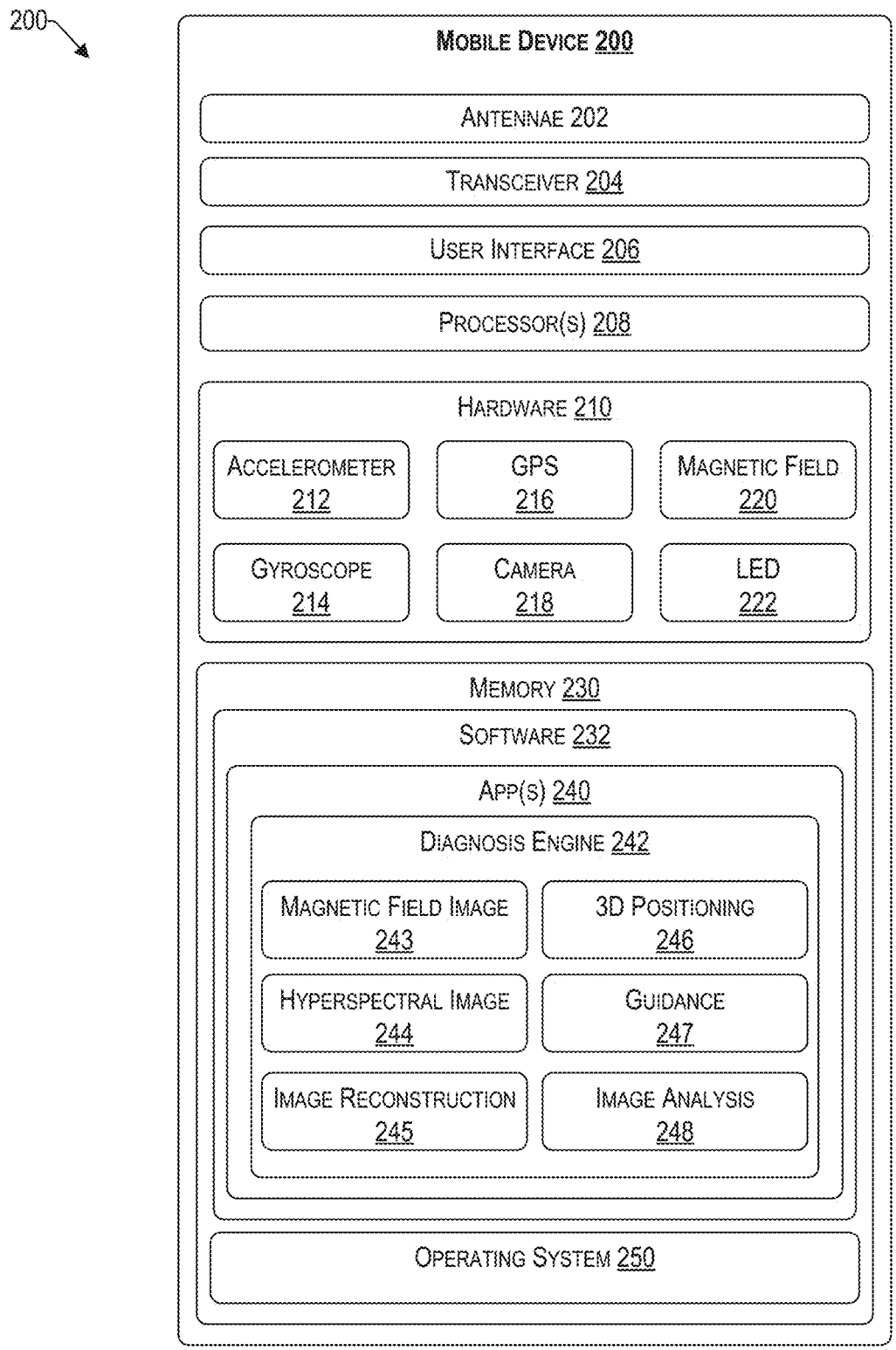
FIG. 2 illustrates a block diagram showing various components of an example mobile device at a high level, consistent with an illustrative embodiment.

As discussed in the context of FIG. 1, the determination of a medical condition of a patient with respect to a target area involves the use of a mobile device. In this regard, FIG. 2 illustrates a block diagram showing various components of an illustrative mobile device 200 at a high level. For discussion purposes, the illustration shows the mobile device 200 in the form of a smartphone device, while it will be understood that other mobile computing devices are contemplated as well.

The mobile device 200 may include one or more antennae 202; a transceiver 204 for cellular, Wi-Fi communication, short-range communication technology, and/or wired communication; a user interface 206; one or more processors 208; hardware 210; and memory 230. In some embodiments, the antennae 202 may include an uplink antenna that sends radio signals to a base station, and a downlink antenna that receives radio signals from the base station. In some other embodiments, a single antenna may both send and receive radio signals. The same or other antennas may be used for Wi-Fi communication and the receipt of magnetic or radio signals that are the response of the body to magnetic fields for magnetic field imaging. These signals may be processed by the transceiver 204, sometimes collectively referred to as a network interface, which is configured to receive and transmit digital data.

In one embodiment, the mobile device 200 includes one or more user interface(s) 206 that enables a user to provide input and receive output from the mobile device 200. For example, the user interface 206 may include a data output device (e.g., visual display(s), audio speakers, haptic device, etc.) that may be used to provide guidance to a user of the mobile device 200 such that the mobile device 200 is properly positioned in 3D space with respect to a target area of a patient. The user interface 206 can also be used to display a representation of a bone, tissue, organ, etc., of the patient as well as a diagnosis of an identified injury based on the 3D representation.

The user interface(s) 206 may also include one or more data input devices. The data input devices may include, but are not limited to, combinations of one or more of keypads, knobs/controls, keyboards, touch screens, microphones, speech recognition packages, and any other suitable devices or other electronic/software selection interfaces.

The mobile device 200 may include one or more processors 208, which may be a single-core processor, a multi-core processor, a complex instruction set computing (CISC) processor, gaming processor, or any other type of suitable processor.

The hardware 210 may include a power source and digital signal processors (DSPs), which may include single-core or multiple-core processors. The hardware 210 may also include network processors that manage high-speed communication interfaces, including communication interfaces that interact with peripheral components. The network processors and the peripheral components may be linked by switching fabric. The hardware 210 may include hardware decoders and encoders, a network interface controller, and/or a USB controller.

The hardware 210 may include various sensors to determine the orientation/position of the mobile device 200. For example, there may be one or more accelerometers 212 that are configured to measure acceleration forces, which may be used to determine an orientation of the mobile device 200. There may be a gyroscope 214, which allows the measure of the rotation of the mobile device, as well as lateral movements. The accelerometer(s) 212 and the gyroscope 214 may be used together to provide guidance as to how to position and the speed of the movement of the mobile device 200.

The hardware 210 may further include a GPS sensor 216 that is operative to provide a location of the mobile device and its speed. In one embodiment, the geographic location, which may include altitude information, may be used to better estimate the expected progress of a medical condition. For example, climate and altitude may be salient in the healing process.

The hardware 210 may include one or more cameras 218 that are operative to take photographs under different lighting conditions, which may be provided at least in part by the LED 222 of the mobile device 200 to capture regular and/or hyperspectral images of a target area of a patient. The one or more cameras 218 may also be used together with the accelerometer(s) 212 and the gyroscope 214 to guide the mobile device 200 to the appropriate position in a 3D space with respect to a target area of the patient. For example, an augmented reality image may be displayed on the user interface with instructions on how to maneuver the mobile device. The resulting images can then be stored in a memory 230 of the mobile device 200 and/or shared with different recipients, such as a patient database, reference database, and/or authorized medical professional, based on permission settings of the diagnosis engine 242.

Today, mobile devices typically include a magnetic field sensor 220. For example, the magnetic field sensor 220 may be a small-scale microelectromechanical systems (MEMS) device for detecting and measuring magnetic fields. Such magnetic sensor may measure the effects of the Lorentz force.

The mobile device 200 includes a memory 230 that may be implemented using computer-readable media, such as computer storage media. Storage media includes volatile and non-volatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD), high definition video storage disks, or other optical storage, magnetic cassettes, magnetic tape, magnetic disk storage or other magnetic storage devices, or any other non-transmission medium that can be used to store information for access by a computing device.

The memory 230 may store various software components or modules that are executable or accessible by the processor(s) 208 and controller(s) of the mobile device 200. The various components of the memory 230 may include software 232 and an operating system 250. The software 232 may include various applications 240, such as a diagnosis engine 242 having several modules, each configured to control a different aspect of the determination of a medical condition of a subject area of a patient. Each module may include routines, program instructions, objects, and/or data structures that perform tasks or implement abstract data types. For example, there may be a magnetic field image module 243 operative to generating various magnetic field images of a target area of a patient. For example, magnetic field image module 243 of the diagnosis engine 242 may direct the transceiver 204 of the mobile device 200 to emit a weak magnetic field and receive signals in response thereto to create an initial magnetic field image of the target area of the patient. These response signals may be radio and/or magnetic signals resulting from the response of the body to the magnetic field, and can be measured after the field is no longer being applied. The resulting magnetic field image may be of a relatively low quality due to the weak field strength. Its representation and quality are improved using the quality enhancement module described later. In some embodiments, the resulting magnetic field is measured by the magnetic field sensor 220 of the mobile device 200.

The diagnosis engine 242 may include a hyperspectral image module 244 that is operative to generate various hyperspectral images of a target area. In one embodiment, the hyperspectral image module 244 is operative to control the LED 222 light source of the mobile device 200 to generate light at different wavelength to obtain a hyperspectral image of the anatomy being monitored, sometimes referred to herein as the target area. The hyperspectral image module 244 interacts with the camera 218 to capture the hyperspectral images of the target area.

The diagnosis engine 242 may include an image reconstruction module 245 that is operative to combine the one or more magnetic field images from the magnetic field image module 243 and one or more hyperspectral images provided by the hyperspectral image module, and the 3D positioning data to generate a detailed representation of the anatomy with a sufficient amount of detail to be able to discern the current condition of the skin, tissues and/or bone to be able to later diagnose a medical condition of a patient based on the detailed representation. For example, for each of the magnetic field and hyperspectral images, the various sensors discussed herein, such as the accelerometer 212 and the gyroscope 214, provide coordinates with respect to the target area. The 3D position information together with the images are used to generate a 3D representation. In one embodiment, each of the one or more magnetic field images and one or more hyperspectral images will comprise a point cloud in which each pixel of the image has an associated set of x, y, and z coordinates in 3D space. To stitch two images together, different methods for this purpose can be applied. For example, scan matching or particle filtering (as used in robotics), or another similar technique can be applied. In these techniques, the change in 3D position measured by the accelerometer 212 or the gyroscope 214 can be used as a first estimate for the relative positions of the two-point clouds of two images. Thereafter, via several iterations of either of these techniques, the true relative difference in 3D position between two point clouds can be established more exactly, and the two point clouds can be merged into a single, larger point cloud. The point cloud of every subsequent image can be stitched into this single growing point cloud in the same manner. In some embodiments, the image reconstruction module 245 is operative to further enhance the 3D representation of the target area by way of machine learning algorithms, discussed in more detail later.

In one embodiment, there is a 3D positioning module 246 that is operative to determine a position of the mobile device 200 with respect to a target area of a patient. To that end, the 3D positioning module 246 uses various sensors of the mobile device 200, such as the accelerometer 212, gyroscope 214, and/or camera 218 to determine a position of the mobile device 200 in 3D space with reference to the target area of a patient. For example, at time t0, the mobile device 200 acquires one magnetic and one hyperspectral image. At time t1, one additional magnetic and one additional hyperspectral image are generated. By virtue of the positioning module 246, the mobile device 200 is able to track its position (e.g., between t0 and time t1, it moved x degrees around its x-axis, y degrees around its y-axis, and z degrees around its z-axis).

In one embodiment, the diagnosis engine 242 includes a guidance module 247 that is operative to provide guidance as to how to position the mobile device 200 such that it is positioned properly for the capturing of the magnetic field and hyperspectral images. To that end, the guidance module 247 may provide instructions via various hardware 210 components of the mobile device 200, such as the speakers, messages on a display (e.g., user interface 206), augmented reality on the display, haptic signals, or any combination thereof.

In one embodiment, the diagnosis engine 242 includes an image analysis module 248 that is operative to receive the 3D representation of the target area from the image reconstruction module 245 and identify (i.e., diagnose) a status of the medical condition of the target area based on the same. In various embodiments, the diagnosis engine 242 may be independent, or may work together with the patient database 110 and/or reference database 112 discussed before in the context of the architecture 100 of FIG. 1. For example, the image analysis module 248 determines the status of the medical condition of the target area of the patient, performs comparisons between the present state (i.e., medical condition), the previous state, and a reference state (e.g., expected present state based on extrapolations) and provides recommendations (e.g., via the user interface 206 of the mobile device 200).

The operating system 250 may include components that enable the mobile device 200 to receive and transmit data via various interfaces (e.g., user controls, communication interface, and/or memory input/output devices), as well as process data using the processor(s) 208 to generate output. The operating system 250 may include a presentation component that presents the output (e.g., display the data on an electronic display of the mobile device 200, store the data in memory 230, transmit the data to another electronic device, etc.). Additionally, the operating system 250 may include other components that perform various additional functions generally associated with an operating system 250. By virtue of the hardware and software of the mobile device 200, the diagnosis engine 242 transforms the mobile device into an efficient portable medical imaging system and diagnosis device.

Example Block Diagrams

Figure 3:
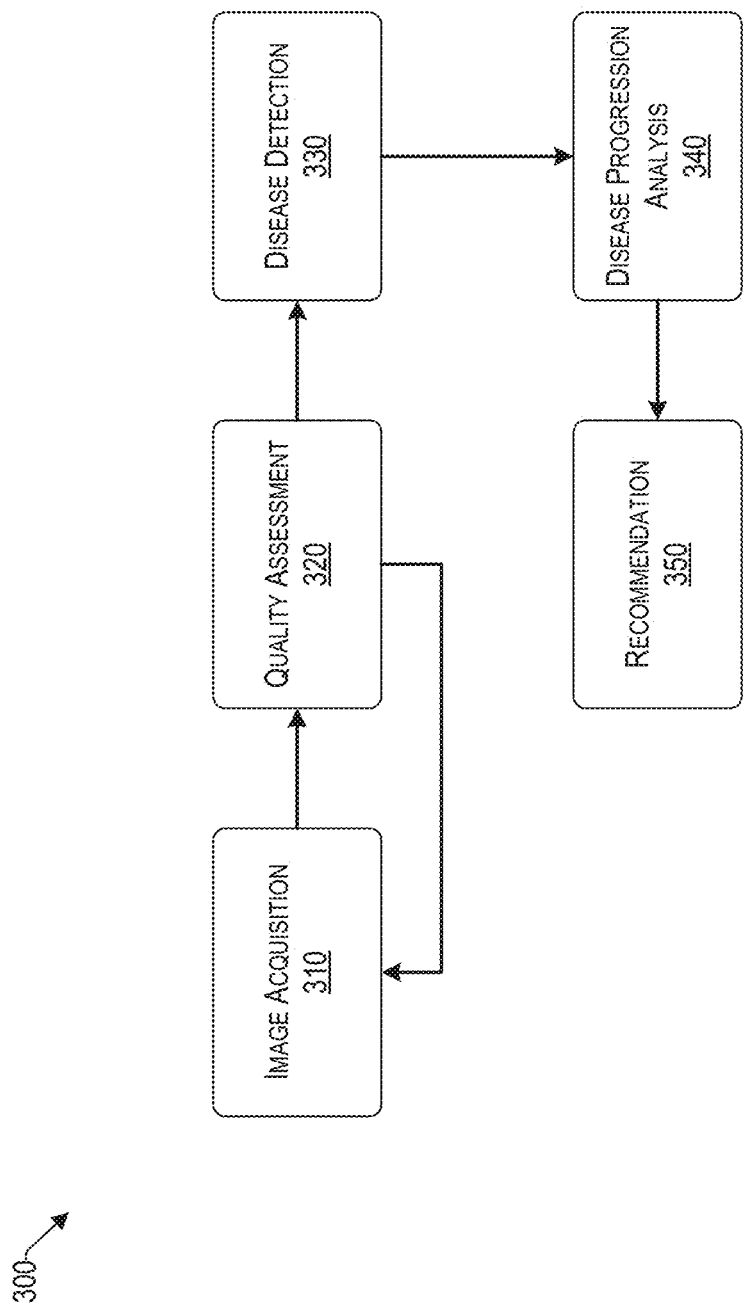
FIG. 3 is a block diagram of a disease detection system, consistent with an illustrative embodiment.

Reference now is made to FIG. 3, which is a block diagram of a disease detection system 300, consistent with an illustrative embodiment. The system 300 includes an image acquisition block 310 that is coupled to a quality assessment block 320. There is a disease detection block 330 coupled to the quality assessment block. There is a disease progression analysis block 340 coupled to the output of the disease detection block 330 and operative to provide an output to a recommendation block 350.

The image acquisition block 310 is operative to capture various images of a target area of a patient by way of a mobile device. The images may be based on magnetic field images and/or hyperspectral images that were taken from different 3D positions relative to a target area of a patient. For example, a diagnosis engine directs a user to move the mobile device to different positions, while inducing a magnetic field and/or light wavelength at various regions of a target area of a patient. These images can be regarded as initial magnetic field and/or initial hyperspectral images.

In one embodiment, at block 320, a quality assessment is performed of each of the images. For example, for each hyperspectral image, the diagnosis engine determines a quality of a resolution of the hyperspectral image. Upon determining that the quality of the resolution of the hyperspectral image is below a predetermined threshold, the image is enhanced by way of a deep learning model. If the resolution of the image cannot be enhanced, the mobile device is guided to an appropriate location in 3D space with respect to the target area, to harvest additional images. A similar approach may be used for each magnetic field image.

The magnetic field image generated by the phone's hardware may be of relatively low quality as compared to professional equipment, since the generated magnetic strength of the transceiver (e.g., in the order of 1000 nT to 6000 nT) is much lower than those used in magnetic resonance imaging machines (greater than 1 T). Upon determining that the image resolution is below a predetermined threshold, to improve image quality, an artificial intelligence module may be used for image enhancement. In one embodiment, the enhancement module conducts image super resolution and quality enhancement directly in an unsupervised manner to improve image resolution and quality. In another embodiment, the enhancement module is based on a convolutional neural network (CNN) that has previously been trained using as training inputs a set of similarly obtained magnetic images, and using as training outputs a set of images obtained using professional equipment. When new low-quality images are obtained, they can be run through this previously trained network to find the previously obtained high quality image that is the closest match. The resulting high quality image may be chosen from a set of pre-existing high quality images, or may be generated using superposition of multiple pre-existing high quality images. Convolutional neural networks and generative adversarial networks are part of the deep learning architecture.

Upon determining that the quality of each image is above a predetermined threshold (or bringing the quality of each picture to above the predetermined threshold as discussed above) a 3D image of the target area is generated based on the one or more magnetic field images and one or more hyperspectral images (which may have been enhanced). In some embodiments, the 3D image generated is further improved using photographs taken by a camera of the mobile device. For example, the photographs may only show the visual exterior of the body part of interest and do not contribute to the interior structure of the 3D image, but they can be used to provide a "skin" for the image which helps to identify how the underlying 3D structure maps to the area of the body under consideration.

At block 330, the generated 3D image is used to diagnose a medical condition (e.g., disease) of the target area. For example, the image may be compared to historic data of different diseases. If the pattern identified in the 3D image is sufficiently similar to one provided in the historical data, then the 3D image is deemed to be consistent with the medical condition of the historical data. In one embodiment, the measure of similarity is conducted by using a deep learning approach in which a neural network has been trained to take as input a 3D image and to output the most likely medical condition, using previously labelled datasets. In another embodiment, a clustering analysis is conducted to group many scans from multiple patients showing similar features into a discrete set of groups that can be labelled as corresponding to a particular condition.

In one embodiment, upon determining the medical condition, at the disease progression analysis block 340, the data of the 3D image is compared to previous scans (e.g., 3D images) to determine the progress in rehabilitation (or lack thereof). There is a recommendation block 350 that may provide feedback on a user interface of the mobile device as to further actions to take in order to improve the identified medical condition.

Figure 4B:
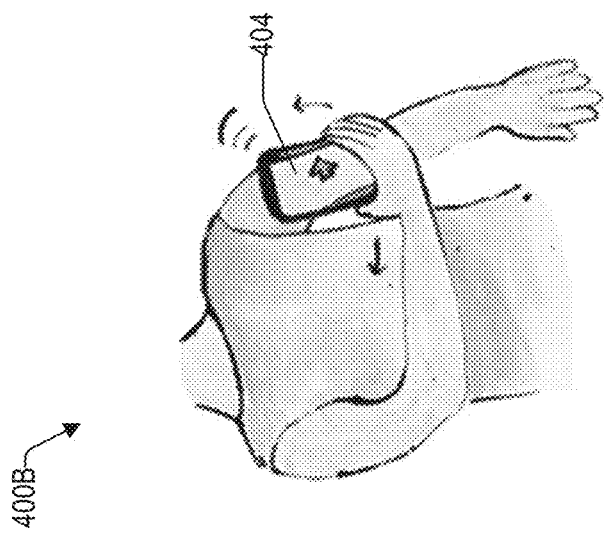
FIG. 4B illustrates a patient receiving instructions from a mobile device to perform a scan of a target area, consistent with an illustrative embodiment.
Figure 4A:
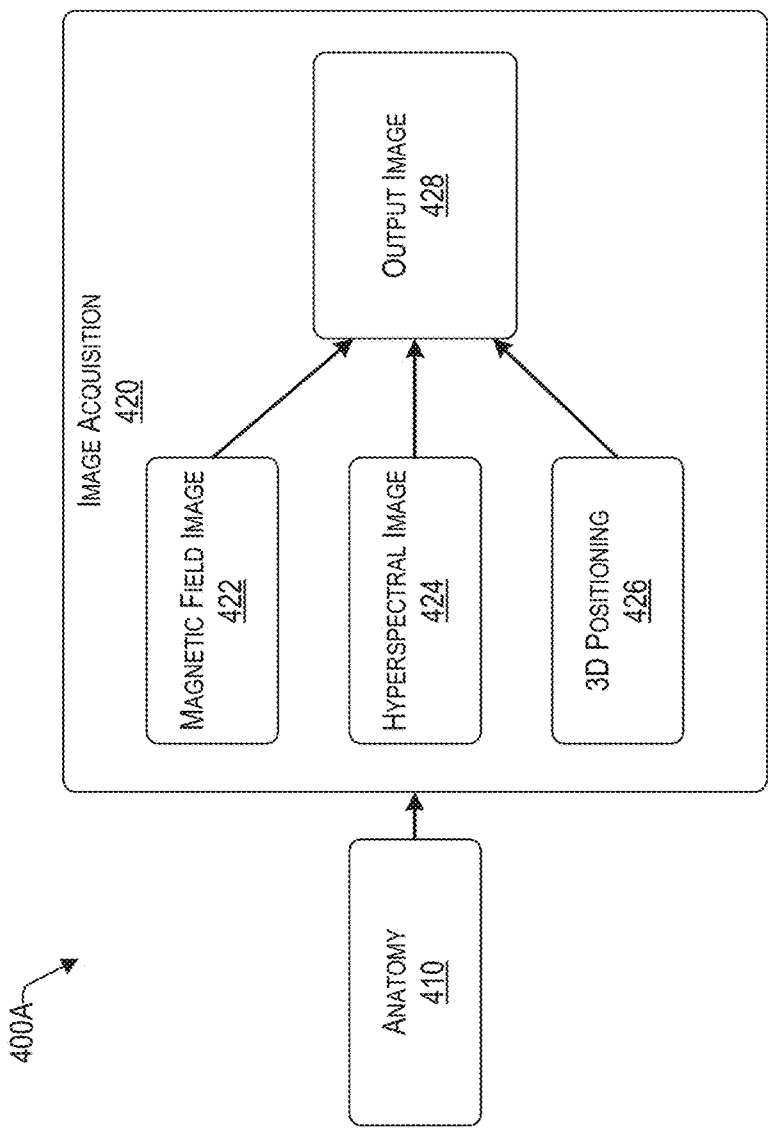
FIG. 4A is a block diagram of an image acquisition block harvesting information from an anatomy of a patient, consistent with an illustrative embodiment.

Reference now is made to FIG. 4A, which is a block diagram 400A of an image acquisition block 420 harvesting information from an anatomy 410 of a patient, consistent with an illustrative embodiment. By way of example and not limitation, the anatomy 410 may be a broken arm of a patient 400B, who is guided by the mobile device 404 to perform a scan of the target area, as illustrated in FIG. 4B. The image acquisition block 420 may include a magnetic field image block 422, a hyperspectral image block 424, a 3D positioning block 426, and an output image block 428. The anatomy 410 of a patient is scanned at a target area by the magnetic field image block 422 and the hyperspectral image block 424. As discussed herein, the magnetic field image block 422 emits a magnetic field and receives signals in response thereto. The response signals are used to create a magnetic field image of the target area of the patient. Similarly, the hyperspectral image block 424 controls a light source of the mobile device 404 to generate light at different wavelength to obtain a hyperspectral image of the anatomy 410 of the target area. The magnetic field images of the magnetic field image block 422, as well as the hyperspectral images of the hyperspectral image block 424 may be harvested from different positions in 3D space with respect to the target area of the patient.

The 3D positioning block 426 uses various sensors discussed herein to record the coordinates (i.e., 3D position in space with respect to the target area of the patient) for each image captured. In this way, the output image block 428 is able to create a 3D image of the anatomy 410 of the patient by combining the information from the magnetic field image block 422, hyperspectral image block 424, and the 3D positioning block 426.

Example Process

Figure 5:
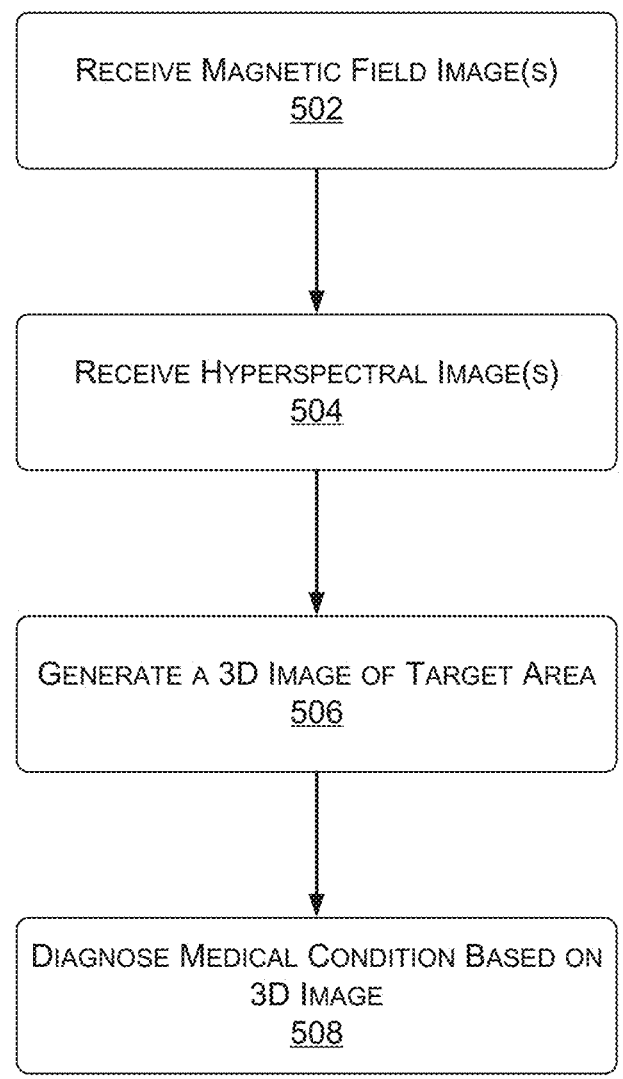
FIG. 5 presents an illustrative process for identifying a medical condition of a target area of a patient by way of a mobile device.

With the foregoing overview of the architecture 100, example mobile device 200, and example disease detection system 300, it may be helpful now to consider a high-level discussion of an example process. To that end, FIG. 5 presents an illustrative process 500 for identifying a medical condition of a target area of a patient by way of a mobile device. Process 500 is illustrated as a collection of blocks in a process, representing a sequence of operations that can be implemented in hardware, software, or a combination thereof. In the context of software, the blocks represent computer-executable instructions that, when executed by one or more processors, perform the recited operations. Generally, computer-executable instructions may include routines, programs, objects, components, data structures, and the like that perform particular functions or implement particular abstract data types. The order in which the operations are described is not intended to be construed as a limitation, and any number of the described blocks can be combined in any order and/or performed in parallel to implement the process. For discussion purposes, the process 500 is described with reference to the architecture 100 of FIG. 1 and the mobile device 200 of FIG. 2.

At block 502, a diagnosis engine 242 of a mobile device 200 receives one or more magnetic field images of a target area of a patient. To that end, the diagnosis engine 242 controls a transceiver 204 of the mobile device 200 such that a magnetic field is emitted onto the target area. Radio and/or magnetic field signals are received from the target area in response to the emitted magnetic field of the transceiver 204.

In one embodiment, the magnetic field signal from the target area is received by a magnetic field sensor 220 of the mobile device 200.

At block 504, one or more hyperspectral images of the target area of the patient are received by the mobile device 200. To that end, the diagnosis engine 242 controls a light source of the mobile device, such as an LED 222, such that light at one or more predetermine wavelengths is generated. A hyperspectral image of an anatomy of the target area is received by a camera 218 of the mobile device 200.

In various embodiments, the magnetic field image(s) and the hyperspectral image(s) may be taken in different order or concurrently from a same position in 3D space with respect to the target area. In some embodiments, a determination is made whether the magnetic field image(s) or the hyperspectral image(s) are sufficient to generate a 3D image rendering of the target area. If not, the diagnosis engine 242 provides guidance on a user interface of the mobile device 200 as to how to position the mobile device 200 in 3D space relative to the target area of the patient.

In some embodiments, each of the images is further enhanced. In this regard, for each image, the diagnosis engine 242 determines a quality of the resolution. If the quality of the resolution is below a predetermined threshold, then the image is enhanced by one or more techniques such as deep learning models, as discussed herein.

At block 506, the diagnosis engine 242 generates a 3D image of the target area based on the received one or more magnetic field images and one or more hyperspectral images, coupled with the 3D position information of each of the images.

At block 508, the diagnosis engine 242 determines the medical condition of the target area based on the generated 3D image.

Example Computer Platform

Figure 6:
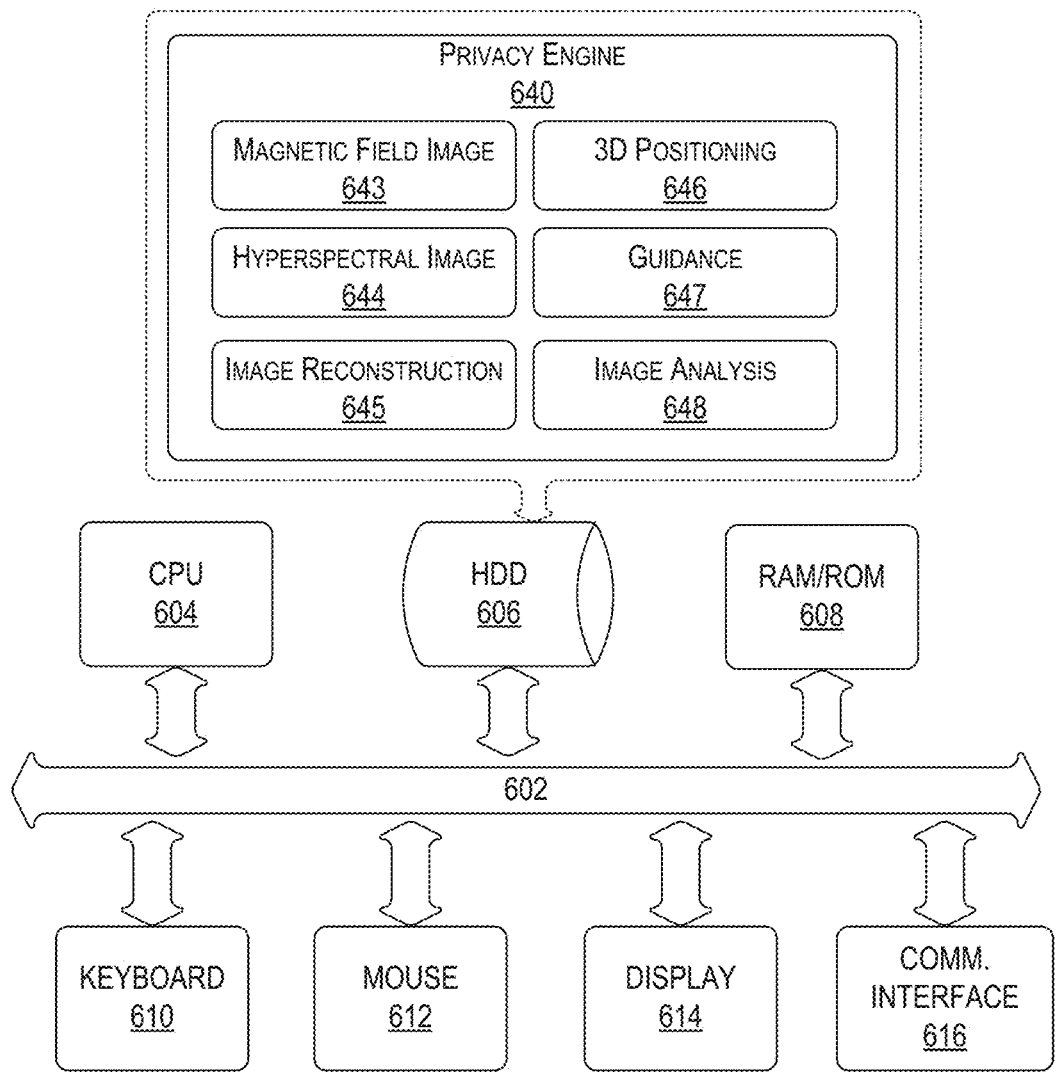
FIG. 6 is a functional block diagram illustration of a computer hardware that can communicate with various networked components.

As discussed above, functions relating to generating a 3D rendering of a target area of a patient and a diagnosis of the medical condition based thereon, as well as other functions discussed herein, can be performed with the use of different types of mobile devices connected for data communication via wireless or wired communication, as shown in FIG. 1. An example mobile device 200 in the form of a smart phone was discussed in the context of FIG. 2. FIG. 6 is a functional block diagram illustration of a computer hardware platform such as a user device, patient database 110, reference database 112, or computing device of an authorized medical professional 120 that can communicate with various networked components.

The computer platform 600 may include a central processing unit (CPU) 604, a hard disk drive (HDD) 606, random access memory (RAM) and/or read only memory (ROM) 608, a keyboard 610, a mouse 612, a display 614, and a communication interface 616, which are connected to a system bus 602.

In one embodiment, the HDD 606, has capabilities that include storing a program that can execute various processes, such as the diagnosis engine 640, in a manner described herein. The diagnosis engine 640 may have various modules configured to perform different functions. For example, there may be a magnetic field image module 643, hyperspectral image module 644, image reconstruction module 645, 3D positioning module 646, guidance module 647, and/or image analysis module 648. Each of these modules was discussed in detail before and will therefore not be repeated here for brevity. In one embodiment, one or more of these modules may be used to control a mobile device remotely over a network. Stated differently, one or more functions discussed in the context of a user device may be delegated to a remote computing device, thereby conserving the computational resources of the mobile device.

In one embodiment, a program, such as Apache™, can be stored for operating the system as a Web server. In one embodiment, the HDD 606 can store an executing application that includes one or more library software modules, such as those for the Java™ Runtime Environment program for realizing a JVM (Java™ virtual machine).

CONCLUSION

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing has described what are considered to be the best state and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The components, steps, features, objects, benefits and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently.

Aspects of the present disclosure are described herein with reference to call flow illustrations and/or block diagrams of a method, apparatus (systems), and computer program products according to embodiments of the present disclosure. It will be understood that each step of the flowchart illustrations and/or block diagrams, and combinations of blocks in the call flow illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the call flow process and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the call flow and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the call flow process and/or block diagram block or blocks.

The flowchart and block diagrams in the Figures illustrate the architecture, functionality, and operation of possible implementations of systems, methods, and computer program products according to various embodiments of the present disclosure. In this regard, each block in the call flow process or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or call flow illustration, and combinations of blocks in the block diagrams and/or call flow illustration, can be implemented by special purpose hardware-based systems that perform the specified functions or acts or carry out combinations of special purpose hardware and computer instructions.

While the foregoing has been described in conjunction with exemplary embodiments, it is understood that the term "exemplary" is merely meant as an example, rather than the best or optimal. Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments have more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A mobile device comprising:
a processor;
a transceiver coupled to the processor;
an accelerometer coupled to the processor;
a gyroscope coupled to the processor;
a storage device coupled to the processor;
a diagnosis engine software stored in the storage device, wherein an execution of the diagnosis engine by the processor configures the mobile device to perform acts comprising:
receiving one or more magnetic field images of a target area of a patient;
receiving one or more hyperspectral images of the target area of the patient;
generating a three-dimensional (3D) image of the target area based on the received one or more magnetic field images, one or more hyperspectral images, and positioning information from at least one of the accelerometer or the gyroscope; and
at least one of diagnosing or monitoring a medical condition of the target area based on the generated 3D image.

2. The mobile device of claim 1, wherein receiving one or more magnetic field images of the target area comprises:
emitting a magnetic field by the transceiver onto the target area; and
receiving at least one of radio or magnetic signals from the target area in response to the emitted magnetic field of the transceiver.

3. The mobile device of claim 2, wherein the magnetic signals from the target area are received by a magnetic field sensor of the mobile device.

4. The mobile device of claim 2, wherein receiving one or more magnetic field images of the target area further comprises, for each of the one or more magnetic field images: the diagnosis engine providing guidance on a user interface of the mobile device as to how to position the mobile device in 3D space with respect to the target area.

5. The mobile device of claim 1, wherein receiving one or more hyperspectral images of the target area comprises, for each hyperspectral image:
controlling a light source of the mobile device, to emit light at one or more predetermined wavelengths; and
recording a hyperspectral image of an anatomy of the target area by a camera of the mobile device.

6. The mobile device of claim 5, wherein receiving one or more hyperspectral images of the target area further comprises, for each of the one or more hyperspectral images: the diagnosis engine providing guidance on the user interface as to how to position the mobile device in 3D space with respect to the target area.

7. The mobile device of claim 1, wherein at least one of the one or more magnetic field images and at least one of the one or more hyperspectral images are taken concurrently from a same position in 3D space with respect to the target area.

8. The mobile device of claim 1, wherein execution of the diagnosis engine further configures the mobile device to perform acts comprising, for each hyperspectral image:
   determining a quality of a resolution of the hyperspectral image; and
   upon determining that the quality of the resolution of the hyperspectral image is below a predetermined threshold, enhancing the image by way of a deep learning model.

9. The mobile device of claim 1, wherein the 3D image is further based on one or more photographs taken by a camera of the mobile device.

10. A non-transitory computer readable storage medium tangibly embodying a computer readable program code having computer readable instructions that, when executed, causes a mobile device to carry out a method, comprising:
   receiving one or more magnetic field images of a target area of a patient;
   receiving one or more hyperspectral images of the target area of the patient;
   for each of the one or more magnetic field images and one or more hyperspectral images, tracking a three-dimensional (3D) position of the phone with respect to the target are of the patient;
   generating a 3D image of the target area based on the received one or more magnetic field images, the one or more hyperspectral images, and the corresponding tracked 3D position of the phone; and
   at least one of diagnosing or monitoring a medical condition of the target area based on the generated 3D image.

11. The non-transitory computer readable storage medium of claim 10, wherein receiving one or more magnetic field images of the target area comprises:
   emitting a magnetic field by a transceiver of the mobile device onto the target area; and
   receiving radio or magnetic signals from the target area in response to the emitted magnetic field of the transceiver.

12. The non-transitory computer readable storage medium of claim 10, wherein the magnetic signals from the target area are received by a magnetic field sensor of the mobile device.

13. The non-transitory computer readable storage medium of claim 10, wherein receiving one or more magnetic field images of the target area further comprises, for each of the one or more magnetic field images: providing guidance on a user interface of the mobile device as to how to position the mobile device in 3D space with respect to the target area.

14. The non-transitory computer readable storage medium of claim 10, wherein receiving one or more hyperspectral images of the target area comprises, for each hyperspectral image:
   controlling a light source of the mobile device, to emit light at one or more predetermined wavelengths; and
   recording a hyperspectral image of an anatomy of the target area by a camera of the mobile device.

15. The non-transitory computer readable storage medium of claim 14, wherein receiving one or more hyperspectral images of the target area further comprises, for each of the one or more hyperspectral images: providing guidance on the user interface as to how to position the mobile device in 3D space with respect to the target area.

16. The non-transitory computer readable storage medium of claim 10, wherein at least one of the one or more magnetic field images and at least one of the one or more hyperspectral images are taken concurrently from a same position in 3D space with respect to the target area.

17. The non-transitory computer readable storage medium of claim 10, further comprising, for each hyperspectral image:
   determining a quality of a resolution of the hyperspectral image; and
   upon determining that the quality of the resolution of the hyperspectral image is below a predetermined threshold, enhancing the image by way of a deep learning model.

18. The non-transitory computer readable storage medium of claim 10, wherein the 3D image is further based on one or more photographs taken by a camera of the mobile device.

19. A computer implemented method, comprising:
   directing a transceiver of a mobile device emit a magnetic field onto a target area of a patient;
   receiving a signal in response to the emitted magnetic field;
   creating one or more magnetic field images of the target area;
   controlling a light emitting source of the mobile device such that light is generated at one or more different wavelengths;
   creating one or more hyperspectral images of the target area in response to the light generated at the one or more different wavelengths;
   tracking a three-dimensional (3D) position of the mobile device with respect to the target area for each of the one or more magnetic field images and one or more hyperspectral images;
   generating a 3D image of the target area based on the created one or more magnetic field images, the one or more hyperspectral images, and the corresponding tracked 3D position of the mobile device; and
   diagnosing a medical condition of the target area based on the generated 3D image.

20. The method of claim 19, further comprising:
   for each of the one or more magnetic field images and the one or more hyperspectral images, determining a quality of the image; and
   upon determining that the image is below a predetermined threshold, enhancing the image by way of a deep learning model.

* * * * *